United States Patent
Govari et al.

(10) Patent No.: US 8,046,049 B2
(45) Date of Patent: Oct. 25, 2011

(54) ROBOTICALLY GUIDED CATHETER

(75) Inventors: Assaf Govari, Haifa (IL); Andres Claudio Altmann, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 523 days.

(21) Appl. No.: 10/785,162

(22) Filed: Feb. 23, 2004

(65) Prior Publication Data
US 2005/0203382 A1    Sep. 15, 2005

(51) Int. Cl.
*A61B 5/05* (2006.01)
(52) U.S. Cl. .......... 600/424; 600/407; 700/245; 901/30; 604/528
(58) Field of Classification Search ................... 600/101, 600/109, 424, 431; 606/2, 130; 901/1, 2, 901/9, 30; 604/528
See application file for complete search history.

(56) References Cited

U.S. PATENT DOCUMENTS

| | | |
|---|---|---|
| 3,470,876 A | 10/1969 | Barchiton |
| 4,173,228 A | 11/1979 | Van Steenwyk et al. |
| 4,475,223 A | 10/1984 | Taniguchi et al. |
| 4,920,980 A | 5/1990 | Jackowski |
| 4,930,494 A | 6/1990 | Takehana et al. |
| 5,078,140 A | 1/1992 | Kwoh |
| 5,125,888 A | 6/1992 | Howard et al. |
| RE34,502 E | 1/1994 | Webster, Jr. |
| 5,339,799 A | 8/1994 | Kami et al. |
| 5,383,852 A * | 1/1995 | Stevens-Wright ......... 604/95.04 |
| 5,391,199 A | 2/1995 | Ben-Haim |
| 5,417,210 A * | 5/1995 | Funda et al. ................... 600/425 |
| 5,431,645 A | 7/1995 | Smith et al. |
| 5,471,982 A | 12/1995 | Edwards et al. |
| 5,489,270 A | 2/1996 | van Erp |
| 5,492,131 A | 2/1996 | Galel |
| 5,546,951 A | 8/1996 | Ben-Haim |
| 5,558,091 A | 9/1996 | Acker et al. |
| 5,562,619 A | 10/1996 | Mirarchi et al. |
| 5,637,090 A * | 6/1997 | McGee et al. ............. 604/95.01 |
| 5,649,956 A | 7/1997 | Jensen et al. |
| 5,657,429 A * | 8/1997 | Wang et al. ................... 700/251 |
| 5,681,260 A | 10/1997 | Ueda et al. |
| 5,696,837 A * | 12/1997 | Green ............................ 382/128 |

(Continued)

FOREIGN PATENT DOCUMENTS

EP    0 776 176 B1    6/1997

(Continued)

OTHER PUBLICATIONS

Bar-Cohen, Yoseph et al., Electroactive Polymers (EAP) Characterization Methods, Proceedings of SPIE's 7th Annual International Symposium on Smart Structures and Materials, Mar. 1-5, 2000, Newport, CA Paper No. 3987-04.

(Continued)

*Primary Examiner* — Brian Casler
*Assistant Examiner* — Jonathan Cwern
(74) *Attorney, Agent, or Firm* — Louis J. Capezzuto

(57) ABSTRACT

Apparatus is provided for use with a steerable catheter that includes a thumb control adapted to control a deflection of a distal tip of the catheter. The apparatus includes a robot, including an end-effector, adapted to be coupled to the thumb control, and a controller, adapted to drive the end-effector to deflect the distal tip by manipulating the thumb control.

30 Claims, 2 Drawing Sheets

U.S. PATENT DOCUMENTS

| | | | |
|---|---|---|---|
| 5,729,129 A | 3/1998 | Acker | |
| 5,752,513 A | 5/1998 | Acker et al. | |
| 5,754,741 A | 5/1998 | Wang et al. | |
| 5,779,623 A | 7/1998 | Bonnell | |
| 5,808,665 A * | 9/1998 | Green | 348/65 |
| 5,833,608 A | 11/1998 | Acker | |
| 5,897,529 A | 4/1999 | Ponzi | |
| 5,938,603 A | 8/1999 | Ponzi | |
| 5,964,757 A | 10/1999 | Ponzi | |
| 6,014,580 A | 1/2000 | Blume et al. | |
| 6,052,618 A | 4/2000 | Dahlke et al. | |
| 6,066,094 A | 5/2000 | Ben-Haim | |
| 6,066,125 A | 5/2000 | Webster, Jr. | |
| 6,083,170 A | 7/2000 | Ben-Haim | |
| 6,123,699 A * | 9/2000 | Webster, Jr. | 604/528 |
| 6,157,853 A | 12/2000 | Blume et al. | |
| 6,165,139 A | 12/2000 | Damadian | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,362 B1 | 4/2001 | Ponzi | |
| 6,210,407 B1 | 4/2001 | Webster Jr. | |
| 6,212,419 B1 | 4/2001 | Blume et al. | |
| 6,226,542 B1 | 5/2001 | Reisfeld | |
| 6,246,200 B1 * | 6/2001 | Blumenkranz et al. | 318/568.11 |
| 6,246,898 B1 * | 6/2001 | Vesely et al. | 600/424 |
| 6,285,898 B1 | 9/2001 | Ben-Haim | |
| 6,301,496 B1 | 10/2001 | Reisfeld | |
| 6,368,285 B1 | 4/2002 | Osadchy et al. | |
| 6,385,476 B1 | 5/2002 | Osadchy et al. | |
| 6,400,980 B1 | 6/2002 | Lemelson | |
| 6,400,981 B1 | 6/2002 | Lillie et al. | |
| 6,402,719 B1 | 6/2002 | Ponzi et al. | |
| 6,425,865 B1 * | 7/2002 | Salcudean et al. | 600/437 |
| 6,436,107 B1 | 8/2002 | Wang et al. | |
| 6,441,577 B2 * | 8/2002 | Blumenkranz et al. | 318/568.11 |
| 6,461,372 B1 | 10/2002 | Jensen et al. | |
| 6,470,205 B2 | 10/2002 | Bosselmann et al. | |
| 6,475,223 B1 | 11/2002 | Werp et al. | |
| 6,490,467 B1 | 12/2002 | Bucholz et al. | |
| 6,507,751 B2 | 1/2003 | Blume et al. | |
| 6,540,725 B1 * | 4/2003 | Ponzi | 604/272 |
| 6,892,091 B1 | 5/2005 | Ben-Haim et al. | |
| 2002/0087151 A1 | 7/2002 | Mody et al. | |
| 2002/0128636 A1 | 9/2002 | Chin et al. | |
| 2002/0143326 A1 | 10/2002 | Foley et al. | |
| 2004/0254566 A1 * | 12/2004 | Plicchi et al. | 606/1 |
| 2005/0107808 A1 * | 5/2005 | Evans et al. | 606/139 |
| 2007/0062546 A1 | 3/2007 | Viswanathan et al. | |

FOREIGN PATENT DOCUMENTS

| | | |
|---|---|---|
| EP | 0 943 293 A1 | 9/1999 |
| EP | 1 125 549 A2 | 8/2001 |
| WO | WO 94/06349 A1 | 3/1994 |
| WO | WO 97/12557 A1 | 4/1997 |
| WO | WO 97/24981 A2 | 7/1997 |
| WO | WO 98/43530 A1 | 10/1998 |
| WO | WO 99/45994 A1 | 9/1999 |
| WO | WO 02/074178 A2 | 9/2002 |

OTHER PUBLICATIONS

Bar-Cohen, Yoseph, Transition of EAP Material From Novelty to Practical Applications—Are We There Yet? Proceedings of EAPAD, SPIE's 8$^{th}$ Annual International Symposium on Smart Structures and Materials, Mar. 5-8, 2001, Newport, CA Paper No. 4329-02.

Haga, Yoichi, Small Diameter Active Catheter Using Shape Memory Alloy Coils, Extended Summary, Trans. IEE of Japan 120-E (No. 11):509-514 (2000).

Kuhl, Christofer et al., Virtual Endoscopy: From Simulation to Optimization of an Active Endoscope, ESAIM: Proceedings, Nov. 2002, vol. 12, 84-93.

Otsuka, Kazuhiro et al., Science and Technology of Shape-Memory Alloys: New Developments, MRS Buletin 27:91-100 (Feb. 2002).

Razavinejad A., Ionic Polymer Metal Composites, ELE 482 BME Seminar (Mar. 2002).

Pending U.S. Appl. No. 10/029,473, Biosense Webster, Inc.

Pending U.S. Appl. No. 10/029,595, Biosense Webster, Inc.

\* cited by examiner

ROBOTICALLY GUIDED CATHETER

FIELD OF THE INVENTION

The present invention relates generally to invasive medical instruments, and specifically to methods and apparatus for manipulating and steering a catheter for diagnostic and therapeutic purposes.

BACKGROUND OF THE INVENTION

Mechanisms for moving, guiding and/or steering invasive medical instruments, such as catheters, in living tissue for therapeutic, diagnostic and surgical purposes are well known in the art. Technologies have been developed that enable locating and tracking medical devices inserted within the body, including determining the orientation of a point on the device, such as the tip of a catheter. Locating a surgical object within living tissue can be accomplished in a variety of ways, including using various forms of electromagnetic or ultrasound energy. Numerous catheter steering and deflection mechanisms are known in the art.

U.S. Pat. No. 6,083,170 to Ben-Haim, which is assigned to the assignee of the present application and is incorporated herein by reference, describes a flexible, elongate probe having a distal end for insertion through physiological tissue, typically through a lumen in the tissue. The probe includes a sensor, which generates signals indicative of a characteristic of the tissue in a vicinity of the probe, and an alignment mechanism, which deflects the distal end of the probe in response to the signals. The signals may be indicative of obstructions or of the direction of a clear channel in the lumen.

U.S. Pat. No. 5,492,131 to Galel, which is incorporated herein by reference, describes a catheter guided by directional control inside a bodily passage by a servo-type system which includes a sensor to transmit position, orientation or velocity information to a microprocessor which is typically programmed with an error detection algorithm, and a motion control system. The motion control system generates a signal representative of the change in position, orientation or velocity needed to guide the catheter along a prescribed course of travel or in general to continuously adjust its position relative to a target. This signal is transmitted to a directional steering system, a forward drive system, or both, to effect the change. The result is described as a closed-loop servo system capable of automated, preprogrammed advancement and/or positioning of the distal catheter tip through branched and convoluted passages to a site where therapeutic action is needed or from which diagnostic information is sought.

U.S. Pat. No. 5,779,623 to Bonnell, which is incorporated herein by reference, describes a remote-controlled device for selectively positioning a medical instrument within a predetermined region of space. The device includes a clamp having two pivotally mounted sections enabling the clamp to be placed in either an opened position or a closed position. Each section has a drive wheel including an arc-shaped groove which accommodates the medical instrument when the clamp is placed in the closed position. Each of the wheels has a coupling gear positioned and configured to pivot apart when the clamp is placed in the open position with portions of teeth of the gears remaining engaged with each other. One of the drive wheels is directly driven by a motor housed in one of the sections of the clamp.

U.S. Pat. No. 6,436,107 to Wang et al., which is incorporated herein by reference, describes a surgical system that includes a remotely-controlled surgical instrument coupled to a tool driver that can spin and actuate the instrument. The instrument includes an actuator rod that is coupled to an end-effector and detachably connected to a push rod. The push rod can move relative to the handle to actuate the end-effector. The handle can be secured to the tool driver by inserting pins into corresponding slots that are located on both the instrument and the tool driver.

U.S. Pat. No. 5,754,741 to Wang et al., which is incorporated herein by reference, describes a robotic system that moves a surgical instrument in response to the actuation of a foot pedal that can be operated by the foot of a surgeon. The robotic system has an end-effector that is adapted to hold a surgical instrument such as an endoscope. The end-effector is coupled to a robotic arm assembly which can move the endoscope relative to the patient. The system includes a computer which controls the movement of the robotic arm in response to input signals received from the foot pedal.

U.S. Pat. Nos. 5,649,956 and 6,461,372 to Jensen et al., which are incorporated herein by reference, describe techniques for releasably holding a surgical instrument, such as an endoscopic instrument configured for delivery through a small percutaneous penetration in a patient. The instrument comprises an elongate shaft with a pair of mounting pins laterally extending from the shaft between its proximal and distal ends. An instrument holder comprises a support having a central bore and an axially extending slot for receiving the instrument shaft and the mounting pins. A pair of locking slots are cut into the support transversely to and in communication with the axial slot so that the mounting pins can be rotated within the locking slots. The instrument support further includes a latch assembly for automatically locking the mounting pins within the locking slots to releasably couple the instrument to the instrument holder. With this twist-lock motion, the surgeon is described as being able to rapidly engage and disengage various instruments from the holder during a surgical procedure, such as open surgery, laparoscopy or thoracoscopy.

PCT Publication WO 99/45994 to Beyar, which is incorporated herein by reference, describes a remote control catheterization system including a propelling device, which controllably inserts a flexible, elongate probe into the body of a patient. A control console, in communication with the propelling device, includes user controls which are operated by a user of the system remote from the patient to control insertion of the probe into the body by the propelling device.

US Patent Application Publication 2002/0143326 to Foley et al., which is incorporated herein by reference, describes techniques for assisting a surgeon in ablating conduction paths in tissue, such as heart tissue. A device can be configured to operate as a template that adheres to the tissue surface, and allows the surgeon to more easily sever the conduction path to form a lesion in a desired location. In particular, the template can be used to guide the surgeon's use of a surgical instrument along a desired ablation path. In some cases, the template may incorporate hardware that structurally supports the instrument for travel along the ablation path.

U.S. Pat. No. RE 34,502 to Webster, Jr., which is incorporated herein by reference, describes a catheter comprising a symmetrical cylindrical control handle, an elongate tubular catheter body, and a flexible catheter tip having a lumen offset from the axis of the catheter tip. The control handle comprises a housing having a piston chamber at its distal end. A piston is mounted in the piston chamber and is afforded lengthwise movement. The proximal end of the catheter body is fixedly attached to the distal end of the piston. A puller wire is attached to the housing and extends through the piston, through and coaxial with the catheter body and into the offset lumen of the catheter tip where it is attached to the wall of the catheter tip. Lengthwise movement of the piston relative to the housing results in deflection of the catheter tip.

U.S. Pat. No. 6,210,407 to Webster, Jr., which is incorporated herein by reference, describes a bi-directional catheter comprising an elongated body, a tip section and a control handle. The body has at least one lumen extending therethrough. The tip section is mounted at the distal end of the catheter body and has at least two diametrically-opposed off-axis lumens, the first smaller than the second. The control handle comprises at least two members longitudinally movable between first and second positions. The catheter further comprises first and second puller wires. The proximal end of each puller wire is connected to an associated movable member of the control handle. Each puller wire extends from the control handle through a lumen of the catheter body. The first puller wire extends into the first lumen in the tip section, and the second puller wire extends into the second lumen in the tip section. The distal end of each puller wire is anchored to the tip section. Proximal movement of a movable member relative to the catheter body results in proximal movement of the puller wire associated with that movable member relative to the catheter body, and thus deflection of the tip section in the direction of the lumen in which that puller wire extends.

U.S. Pat. Nos. 6,066,125 and 6,123,699 to Webster, Jr., which are incorporated herein by reference, describe omnidirectional steerable catheters, and U.S. Pat. Nos. 6,183,463 and 6,198,974 to Webster, Jr., which are incorporated herein by reference, describe bi-directional steerable catheters.

U.S. Pat. No. 3,470,876 to Barchilon, which is incorporated herein by reference, describes a steerable catheter with a distal end that is guidable through 360 degrees by means of four guide lines extending along the length of the catheter and differentially operated in pairs.

U.S. Pat. No. 4,920,980 to Jackowski, which is incorporated herein by reference, describes a catheter having a wire member loosely positioned in a bore thereof. The wire member is secured to the catheter at a position adjacent the distal end, such position being radially spaced from the axis of the catheter. The wire member extends through the bore and out of the proximal end of the catheter, so that the distal end of the catheter can be bent by pulling the wire member.

U.S. Pat. No. 5,489,270 to van Erp; U.S. Pat. Nos. 5,897,529, 5,938,603, 5,964,757, 6,171,277 and 6,210,362 to Ponzi; U.S. Pat. No. 6,402,719 to Ponzi et al.; and U.S. Pat. No. 6,165,139 to Damadian, all of which are incorporated herein by reference, describe steerable catheters.

U.S. Pat. No. 4,930,494 to Takehana et al., which is incorporated herein by reference, describes an endoscope that is bent using a shape memory alloy (SMA). The distal end of an insertion section of the endoscope is divided into a plurality of segments, each of which includes a pair of SMA coils which are arranged symmetrically with respect to an axis and memorize a close-winding shape. As the SMA coils recovers their memorized shape, the distal end of the insertion section is bent. The SMA coils are restored to the memorized shape when they are conductively heated by means of a current supply circuit. The current supply circuit comprises an input unit for inputting a target value of the bend angle for a leading segment, a sensor for detecting the distance of insertion of the insertion section, a detector circuit for detecting the bend angle of each segment, and means for controlling the amount of current supply so that the bend angle of the SMA coils agrees with a target angle. The inputted angle is set as the target angle for the leading segment, and the detected bend angle of each segment is set as the target angle for each succeeding segment. The set value is renewed each time the insertion distance of the insertion section attains a predetermined distance.

Kühl C et al., in "Virtual endoscopy: from simulation to optimization of an active endoscope," ESAIM: Proceedings 12:84-93 (November 2002), which is incorporated herein by reference, describe a polyarticulated device actuated with SMA springs for endoscopy.

Haga Y et al., in "Small diameter active catheter using shape memory alloy coils," Trans. IEE of Japan 120-E (No.11):509-514 (2000), which is incorporated herein by reference, describe an active catheter having many joints comprising SMA coil actuators.

Otsuka K et al., in "Science and technology of shape-memory alloys: new developments," MRS. Bulletin 27:91-100 (February 2002), which is incorporated herein by reference, present an overview of recent progress in the field of SMAs, including a discussion of fundamental SMA concepts, and examples of applications.

Bar-Cohen Y, in "Transition of EAP material from novelty to practical applications—are we there yet?" Proceedings of EAPAD, Paper No. 4329-02 (March 2001), which is incorporated herein by reference, presents a review of current efforts-and challenges in the-field of electroactive polymers (EAPs), including the use of EAPs for catheter steering elements.

Bar-Cohen Y et al., in "Electroactive polymers (EAP) characterization methods," Proceedings of SPIE's 7th Annual International Symposium on Smart Structures and Materials, Paper No. 3987-04 (March 2000), which is incorporated herein by reference, describe a new testing procedure for bending EAPs, in order to quantify their electrical and mechanical properties.

Razavinejad A, in "Ionic polymer metal composites," ELE 482 BME Seminar (March 2002), which is incorporated herein by reference, presents an overview of ionic electroactive polymers (ionic EAPs, also known as ionic polymer metal composites (IPMCs)), which bend in response to an electrical activation as a result of the mobility of cations in the polymer network.

PCT Publication WO 98/43530 to Zilberstein et al., which is assigned to the assignee of the present invention and is incorporated herein by reference, describes an elongate probe having a longitudinal axis and a distal tip, and including at least one deflection mechanism, which includes an elastic flexible member, having distal and proximal ends and having a predetermined bending stiffness. The flexible member is fixed within the probe generally parallel to the longitudinal axis thereof. The probe further includes a pull wire having a distal end coupled to the distal end of the flexible member, and a proximal end that is tensioned longitudinally to deflect the probe.

U.S. Pat. No. 6,246,898 to Vesely et al., which is incorporated herein by reference, describes a method for carrying out a medical procedure using a 3-D tracking and imaging system. A surgical instrument, such as a catheter, probe, sensor, pacemaker lead, needle, or the like is inserted into a living being, and the position of the surgical instrument is tracked as it moves through a medium in a bodily structure. The location of the surgical instrument relative to its immediate surroundings is displayed to improve a physician's ability to precisely position the surgical instrument. The method is described as being able to be integrated with robotic surgery.

U.S. Pat. No. 6,470,205 to Bosselmann et al., which is incorporated herein by reference, describes a medical instrument for insertion into an examination subject, having an elongated instrument body formed by a number of successively arranged rigid sections, with respective, successive sections being connected to one another via articulated joints which can be angled relative to one another. The instrument is either fashioned in the nature of a robot arm, or as an instrument to be manually guided.

PCT Publication WO 02/074178 to Brock et al., which is incorporated herein by reference, describes a remotely controllable flexible instrument system for performing a medical procedure on a subject. The instrument system comprises: an instrument shaft having proximal and distal ends, the shaft being insertable into a subject so as to dispose the distal end of the instrument shaft internally within a subject; a shaft mount coupled to the instrument shaft at the proximal end of the instrument shaft; and a drive unit drivably coupled to the shaft mount. The instrument shaft comprises an elongated shaft that supports a medical procedure mechanism for performing the medical procedure at an internal target site. The elongated shaft is constructed and arranged such that some length of the shaft is inherently and sufficiently deformable so as to readily flex and pass atraumatically through an anatomic passage of the subject. The instrument further includes a remote user interface having a user input device connected to an electrical controller which receives commands from the user input device and transmits signals to the drive unit in accordance with manipulations of the user input device by a user. The electrical controller includes a command processing mechanism for controlling bending of one or more deformable lengths of the elongated shaft and movement of the medical procedure mechanism in accordance with manipulations of the user input device by the user.

U.S. Pat. No. 5,808,665 to Green, which is incorporated herein by reference, describes a teleoperator system with telepresence. The system includes right and left hand controllers for control of right and left manipulators through use of a servomechanism that includes a computer. The teleoperator system comprises an endoscopic surgical instrument suited for endoscopic surgery. The surgical instrument comprises a control servomechanism which operates an insertion section. The insertion section comprises a forearm, a wrist and an end-effector. The end-effector is a modified surgical instrument such as retractors, electrosurgical cutters, electrosurgical coagulators, forceps, needle holders, scissors, blades and irrigators.

U.S. Pat. No. 5,339,799 to Kami et al., which is incorporated herein by reference, describes a medical system comprising a medical apparatus including an operation unit manipulated by a surgeon and a treatment section formed away from the operation unit for treating a subject, a detector or a pressure sensor for detecting a state of contact between the subject and the treatment section, and a reproduction mechanism for amplifying a small contact pressure according to the output of the detector and thus reproducing the state of contact so that the surgeon can perceive the state of contact.

US Patent Application Publication 2002/0128636 to Chin et al., which is incorporated herein by reference, describes techniques for positioning a medical instrument at a desired biological target tissue site. The system includes an elongated sheath having a deflectable distal end configured to deflect or otherwise position at least a portion of a medical instrument during a surgical procedure, allowing for the placement of the deflected portion adjacent or proximate to a predetermined target tissue surface. The positioning system may be incorporated into the medical instrument. The medical instrument may be an ablation system. The medical instrument may be controlled by a robot during a robotic minimally invasive surgical procedure. The robot can telescopically translate or rotate the medical instrument in order to position the ablation sheath and the ablation element correctly to produce the ablation of tissue.

U.S. Pat. No. 5,078,140 to Kwoh, which is incorporated herein by reference, describes a method for computer-controlled stereotactic surgery. The method utilizes an imaging device, a robotic arm, and a means for controlling the robotic arm. The imaging device provides information regarding the structure of the bodily location to be operated on. The robotic arm is utilized to precisely orient the surgical tools or other implements used in conducting the surgery or related procedure. The control means, such as a computer, utilizes information received from the imaging device, alone or together with other information, to control the robotic arm.

U.S. Pat. No. 6,490,467 to Bucholz et al., which is incorporated herein by reference, describes a system for use during a medical or surgical procedure on a body. The system generates an image representing the position of one or more body elements during the procedure using scans generated by a scanner prior to or during the procedure. The image data set has reference points for each of the body elements, the reference points of a particular body element having a fixed spatial relation to the particular body element. The system includes an apparatus for identifying, during the procedure, the relative position of each of the reference points of each of the body elements to be displayed.

US Patent Application Publication 2002/0087151 to Mody et al., which is incorporated herein by reference, describes techniques for ablating a selected portion of a contact surface of biological tissue. The system includes an elongated ablation sheath having a preformed shape adapted to substantially conform a predetermined surface thereof with the contact surface of the tissue. The ablation sheath defines an ablation lumen sized to slidably receive an elongated ablative device longitudinally therethrough. The ablative device includes a flexible ablation element selectively generating an ablative field sufficiently strong to cause tissue ablation. Advancement of the ablation element slidably through the ablation lumen of the ablation sheath selectively places the ablation element along the ablation path for guided ablation on the contact surface when the predetermined surface is in suitable contact therewith. The ablation sheath or ablation element can be controlled by a robot during a robotic minimally-invasive surgical procedure. The robot can telescopically translate or rotate the ablation sheath or ablation element in order to position the ablation sheath and the ablation element correctly to produce the ablation of tissue.

U.S. Pat. No. 6,400,980 to Lemelson, which is incorporated herein by reference, describes a computerized imaging system that is employed to sense the position of an endoscopic treatment system within the body of a patient. In a preferred embodiment, the system provides real-time computer control to maintain and adjust the position of the treatment system and/or the position of the patient relative to the treatment system; and also optionally provides real-time computer control of the operation of the treatment system itself. Other embodiments include a steerable catheter system having a rotatable abrasive member actuated by an external magnetic field.

U.S. Pat. No. 5,681,260 to Ueda et al., which is incorporated herein by reference, describes guiding apparatus for guiding an insertable body within an inspected object. The guiding apparatus comprises a guided part and a guiding device provided outside the inspected object, adapted to magnetically guide the guided part. The guiding device includes a driving device for moving the guiding part at least two-dimensionally.

U.S. Pat. Nos. 6,507,751, 6,014,580, 6,212,419, and 6,157,853 to Blume et al., which are incorporated herein by reference, describe methods, including interactive displays, of modifying magnetic fields to move or guide surgically implanted objects which comprise magnetic material.

U.S. Pat. No. 6,475,223 to Werp et al., which is incorporated herein by reference, describes a method for moving an implant in the body by applying mechanical pushing forces and magnetically steering the implant on a predetermined path by means of making changes in an externally applied magnetic system.

U.S. Pat. No. 5,125,888 to Howard et al., which is incorporated herein by reference, describes a method of observing the location and movement of a magnetic object within the body, employing magnetic systems.

U.S. Pat. No. 4,173,228 to Van Steenwyk et al.; U.S. Pat. Nos. 5,558,091, 5,729,129, and 5,752,513 to Acker et al.; and U.S. Pat. No. 5,833,608 to Acker, all of which are incorporated herein by reference, describe methods and apparatus for magnetic determination of position and orientation.

U.S. Pat. Nos. 5,546,951 and 6,066,094 to Ben-Haim, and European Patent 0 776 176 to Ben-Haim et al., which are assigned to the assignee of the present patent application and are incorporated herein by reference, describe methods for sensing an electrical property of heart tissue, for example, local activation time, as a function of the precise location within the heart. The data are acquired with a catheter that has electrical and location sensors in its distal tip, and which is advanced into the heart. Techniques for sensing cardiac electrical activity are also described in U.S. Pat. No. 5,471,982 to Edwards et al., commonly-assigned U.S. Pat. Nos. 5,391,199 and 6,066,094 to Ben-Haim, U.S. Pat. No. 6,052,618 to Dahlke et al., and in PCT Patent Publications WO 94/06349 and WO 97/24981, which are incorporated herein by reference.

Methods of creating a map of the electrical activity of the heart based on these data are disclosed in U.S. Pat. Nos. 6,226,542 and 6,301,496 to Reisfeld, which are assigned to the assignee of the present patent application and are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, which alters the propagation of the heart's electrical activity and restores normal heart rhythm. Methods for constructing a cardiac map of the heart are also disclosed in U.S. Pat. Nos. 5,391,199 and 6,285,898 to Ben-Haim, and in U.S. Pat. Nos. 6,368,285 and 6,385,476 to Osadchy et al., which are assigned to the assignee of the present patent application and are incorporated herein by reference.

European Patent Application EP 1 125 549 and corresponding U.S. patent application Ser. No. 09/506,766 to Ben-Haim et al., which are assigned to the assignee of the present patent application and are incorporated herein by reference, describe techniques for rapidly generating an electrical map of a chamber of the heart. The catheter used for these techniques comprises a contact electrode at the distal tip of the catheter and an array of non-contact electrodes on the shaft of the catheter near the distal end. The catheter also comprises at least one position sensor. Information from the non-contact electrodes and contact electrode is used for generating a geometric and electrical map of the cardiac chamber.

SUMMARY OF THE INVENTION

In embodiments of the present invention, a robotic guided catheter system comprises a catheter, a control mechanism, and a console. The catheter typically comprises at least one position sensor located in a vicinity of a distal tip of the catheter. During a medical procedure, the catheter is inserted into an area of interest of a subject, such as a body cavity (e.g., a heart) or a physiological lumen (e.g., a blood vessel or a digestive tract), and the console generates a map of the area of interest. A user of the system indicates a position at which the distal tip is to be positioned, and the console drives the control mechanism to position the distal tip at the desired position.

In some embodiments of the present invention, the catheter comprises a human-controllable steerable catheter capable of being manually manipulated by a user, such as catheters that are widely commercially available and used today. The control mechanism comprises manually-controllable means for deflecting the distal tip of the catheter, such as a control handle and/or a thumb control. The control mechanism further comprises a robotic control mechanism, which is adapted to hold and manipulate the catheter by generally mimicking the motions of a hand of a surgeon.

In some embodiments of the present invention, the catheter comprises an automated catheter, adapted to be primarily robotically controlled. The control mechanism comprises an integrated robotic control mechanism, which comprises a plurality of puller wires, e.g., four. The puller wires are disposed about the circumference of the catheter and extend along its length, typically passing through respective lumens. The distal ends of the puller wires are attached at respective points in a vicinity of the distal end of the catheter, and the proximal ends of the wires are coupled to respective motors. The motors are able to tense and relax the respective puller wires. Typically, by selective activation of respective motors, the control mechanism is able to manipulate the distal end of the catheter through 360 degrees of deflection. Alternatively, the integrated robotic control mechanism comprises a steering mechanism that utilizes shape memory alloys (SMAs), electroactive polymers (EAPs), and/or ionic polymer metal composites (IPMCs).

In some embodiments of the present invention, the position sensor is adapted to generate six dimensions of location and orientation information, typically continuously. The console is adapted to determine the roll of the catheter in a vicinity of the distal tip thereof, by using the six dimensions of information. The control mechanism and the catheter typically comprise robotic means for deflecting the distal tip in either (a) a single direction, for any given roll of the distal tip, or (b) in two opposing directions, for any given roll of the distal tip. In order to position the distal tip at a desired target, the console is adapted to: drive the control mechanism to robotically move the distal tip into a vicinity of the target; roll the catheter so that the target intersects a curve defined by the points to which the distal tip is able to deflect, given the roll of the distal tip; and deflect the distal tip to the target.

In some embodiments of the present invention, when the control mechanism attempts to roll the distal tip of the catheter, rotation of a proximal end of the catheter in a vicinity of the control mechanism sometimes does not translate into equivalent roll of the distal tip. For example, the distal tip may sometimes become slightly caught on tissue of the area of interest. As the control mechanism rotates the proximal end, torque builds up in the catheter, until the torque is sufficient to cause the distal tip to come free from the tissue and rotate suddenly. In some embodiments of the present invention, the position sensor is adapted to generate six dimensions of location and orientation information, typically continuously. The console is adapted to determine the roll of the catheter in a vicinity of the distal tip, by using the six dimensions of information. When the console drives the control mechanism to rotate the catheter, the console substantially simultaneously determines the roll of the distal tip, and compares this roll with the expected roll based on the known rotation of the proximal end of the catheter. If the console detects a lag of the roll of the distal tip with respect to the rotation of the proximal end of the catheter, the console drives the control mechanism to attempt to move the distal tip in order to free the distal tip from tissue on which the tip is presumably caught. For example, the console may drive the control mechanism to:

(a) straighten and/or deflect the distal tip, (b) jiggle the distal tip until it comes free from the tissue, such as by quickly, repeatedly, rhythmically or irregularly rotating the proximal end back and forth by a few degrees, (c) translationally move the distal tip back and forth (e.g., left/right, up/down), and/or (d) advance and/or withdraw the distal tip.

There is therefore provided, in accordance with an embodiment of the present invention, apparatus for use with a steerable catheter that includes a thumb control adapted to control a deflection of a distal tip of the catheter, the apparatus including a robot, including:

an end-effector, adapted to be coupled to the thumb control; and a controller, adapted to drive the end-effector to deflect the distal tip by manipulating the thumb control.

For some applications, the controller is adapted to drive the end-effector to deflect the distal tip by moving the thumb control longitudinally with respect to a longitudinal axis of the catheter.

For some applications, the catheter includes a handle, adapted to control a roll of the distal tip; the robot includes a handle end-effector, adapted to be coupled to the handle; and the controller is adapted to drive the handle end-effector to roll the distal tip by manipulating the handle. Alternatively or additionally, the catheter includes a handle, adapted to advance and withdraw the catheter; the robot includes a handle end-effector, adapted to be coupled to the handle; and the controller is adapted to drive the handle end-effector to perform, by manipulating the handle, at least one action selected from the list consisting of: advancing the catheter and withdrawing the catheter.

In an embodiment of the present invention, the apparatus includes a computer pointing device, adapted to receive an indication of a desired position of the distal tip; the catheter includes a position sensor, fixed in a vicinity of the distal tip, and adapted to generate a position signal; and the controller is adapted to receive the position signal, and, responsive thereto, to drive the end-effector to position the distal tip at the desired position.

There is further provided, in accordance with an embodiment of the present invention, apparatus including:

a steerable catheter, including a thumb control, which is adapted to control a deflection of a distal tip of the catheter; and a robot, including:

an end-effector, adapted to be coupled to the thumb control; and a controller, adapted to drive the end-effector to deflect the distal tip by manipulating the thumb control.

There is also provided, in accordance with an embodiment of the present invention, apparatus for use with a steerable catheter that includes controls adapted to control a deflection of a distal tip of the catheter, which controls are generally optimized for manipulation by a human hand, the apparatus including a robot, including:

at least one end-effector, adapted to be coupled to at least a portion of the controls; and a controller, adapted to drive the at least one end-effector to deflect the distal tip by inducing motion of the portion of the controls that generally mimics motion of the portion of the controls induced when a human hand manipulates the controls.

For some applications, the controller is adapted to drive the end-effector to deflect the distal tip by moving the portion of the controls longitudinally with respect to a longitudinal axis of the catheter.

For some applications, the controls are adapted to control a roll of the distal tip; the robot includes a roll end-effector, adapted to be coupled to the controls; and the controller is adapted to drive the roll end-effector to roll the distal tip by inducing motion of the controls that generally mimics motion of the controls induced when a human hand manipulates the controls. Alternatively or additionally, the controls are adapted to advance and withdraw the catheter; the robot includes a longitudinal motion end-effector, adapted to be coupled to the controls; and the controller is adapted to drive the longitudinal motion end-effector to perform, by inducing motion of the controls that generally mimics motion of the controls induced when a human hand manipulates the controls, at least one action selected from the list consisting of: advancing the catheter and withdrawing the catheter.

In an embodiment of the present invention, the apparatus includes a computer pointing device, adapted to receive an indication of a desired position of the distal tip; the catheter includes a position sensor, fixed in a, vicinity of the distal tip, and adapted to generate a position signal; and the controller is adapted to receive the position signal, and, responsive thereto, to drive the end-effector to position the distal tip at the desired position.

There is additionally provided, in accordance with an embodiment of the present invention, apparatus including:

a steerable catheter, including controls adapted to control a deflection of a distal tip of the catheter, which controls are generally optimized for manipulation by a human hand; and a robot, including:

at least one end-effector, adapted to be coupled to at least a portion of the controls; and a controller, adapted to drive the at least one end-effector to deflect the distal tip by inducing motion of the portion of the controls that generally mimics motion of the portion of the controls induced when a human hand manipulates the controls.

There is yet additionally provided, in accordance with an embodiment of the present invention, apparatus including:

a steerable catheter, including:

a distal tip adapted to be controllably deflectable in no more than two directions for any given rotation of the distal tip, such that a set of all points to which the tip can be deflected at the given rotation forms a deflection curve for the given rotation; and a position sensor, fixed in a vicinity of the distal tip, and adapted to generate a position signal;

a robot, adapted to manipulate a proximal end of the catheter; and a control unit, adapted to:
receive the position signal, and
position the distal tip at a target by driving the robot to:
  position the distal tip in a vicinity of the target, responsive to the position signal,
  rotate the proximal end in order to cause the distal tip to roll to a rotation the deflection curve of which includes the target, the rotation determined responsive to the position signal, and
  deflect the distal tip along the deflection curve to the target.

For some applications, the distal tip is adapted to be controllably deflected in no more than one direction for the given rotation of the distal tip. For some applications, the control unit is adapted to position the distal tip in the vicinity of the target by positioning the distal tip so that the deflection curve of at least one rotation of the distal tip includes the target.

In an embodiment of the present invention, the apparatus includes a computer pointing device, adapted to receive an indication of a position of the target, and the control unit is adapted to drive the robot to position the distal tip at the position of the target, responsive to the position signal.

For some applications, the position sensor is adapted to generate the position signal having six dimensions of position and orientation information.

There is still additionally provided, in accordance with an embodiment of the present invention, apparatus including:
  a steerable catheter having a distal tip, the catheter including a position sensor, fixed in a vicinity of the distal tip, and adapted to generate a position signal;
  a robot, adapted to be coupled to a proximal end of the catheter; and
  a control unit, adapted to:
    drive the robot to apply rotation to the proximal end of the catheter,
    receive the position signal,
    responsive to the position signal, determine a roll of the distal tip, and
    responsive to a determination that the roll lags the rotation, drive the robot to move a portion of the proximal end of the catheter.

For some applications, the control unit is adapted to drive the robot to move the portion of the proximal end of the catheter to perform at least one action selected from the list consisting of: straightening the distal tip and deflecting the distal tip. Alternatively or additionally, the control unit is adapted to drive the robot to move the portion of the proximal end of the catheter to effect translational back and forth motion of the distal tip. Further alternatively or additionally, the control unit is adapted to drive the robot to move the portion of the proximal end of the catheter to perform at least one action selected from the list consisting of: advancing the distal tip and withdrawing the distal tip.

For some applications, the position sensor is adapted to generate the position signal having six dimensions of position and orientation information.

For some applications, the control unit is adapted to move the portion of the proximal end of the catheter to jiggle the distal tip. For example, the control unit may jiggle the distal tip by rotating the proximal end of the catheter.

There is still further provided, in accordance with an embodiment of the present invention, a method for use with a steerable catheter that includes a thumb control adapted to control a deflection of a distal tip of the catheter, the method including:
  coupling a robotic end-effector to the thumb control; and
  driving the end-effector to deflect the distal tip by manipulating the thumb control.

There is also provided, in accordance with an embodiment of the present invention, a method for use with a steerable catheter that includes controls adapted to control a deflection of a distal tip of the catheter, which controls are generally optimized for manipulation by a human hand, the method including:
  coupling at least one robotic end-effector to at least a portion of the controls; and
  driving the at least one end-effector to deflect the distal tip by inducing motion of the portion of the controls that generally mimics motion of the portion of the controls induced when a human hand manipulates the controls.

There is further provided, in accordance with an embodiment of the present invention, a method for use with a steerable catheter having a distal tip adapted to be controllably deflectable in no more than two directions for any given rotation of the distal tip, such that a set of all points to which the tip can be deflected at the given rotation forms a deflection curve for the given rotation, the method including:
  receiving a position signal from a vicinity of the distal tip; and
  robotically positioning the distal tip at a target by:
    robotically positioning the distal tip in a vicinity of the target, responsive to the position signal,
    robotically rotating the proximal end in order to cause the distal tip to roll to a rotation the deflection curve of which includes the target, the rotation determined responsive to the position signal, and
    robotically deflecting the distal tip along the deflection curve to the target.

There is still further provided, in accordance with an embodiment of the present invention, a method for use with a steerable catheter having a distal tip and a proximal end, the method including:
  robotically rotating the proximal end of the catheter;
  receiving a position signal from a vicinity of the distal tip of the catheter;
  responsive to the position signal, determining a roll of the distal tip; and
  responsive to a determination that the roll lags the rotation, robotically moving a portion of the proximal end of the catheter.

The present invention will be more fully understood from the following detailed description of embodiments thereof, taken together with the drawings, in which:

DETAILED DESCRIPTION OF EMBODIMENTS

Figure 1:
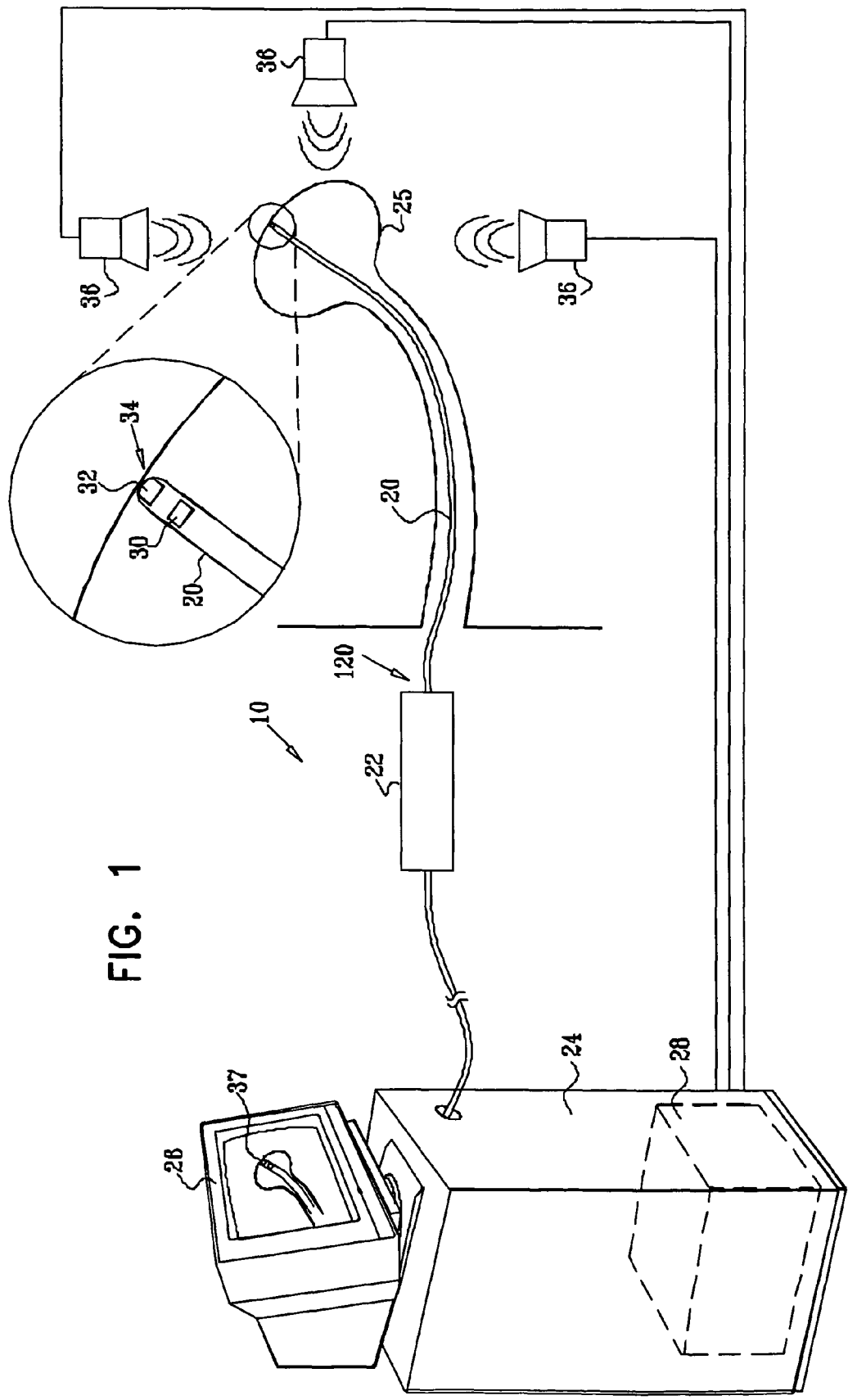
FIG. 1 is a schematic illustration of a robotic guided catheter system, in accordance with an embodiment of the present invention.

FIG. 1 is a schematic illustration of a robotic guided catheter system 10, in accordance with an embodiment of the present invention. Catheter system 10 comprises a catheter 20, a control mechanism 22, and a console 24. Catheter 20 is adapted to be inserted into an area of interest 25 of a subject, such as a body cavity (e.g., a heart) or a physiological lumen (e.g., a blood vessel or a digestive tract). Console 24 typically comprises a display monitor 26 and a computer 28. Computer 28 is programmed in software and/or hardware to carry out the functions described herein. This software may be downloaded to the computer in electronic form, over a network, for example, or it may alternatively be provided on tangible media, such as magnetic or optical media or other non-volatile memory. For some applications, computer 28 comprises a general-purpose computer.

Catheter 20 typically comprises at least one position sensor 30 and at least one tool 32, both located in a vicinity of a distal tip 34 of the catheter. For example, tool 32 may comprise a sensing electrode, an ablating element, a temperature sensor, or an ultrasound transducer.

Position sensor 30 generates or receives signals used to determine the position and orientation of catheter 20. Suitable position sensors are described, for example, in the above-referenced U.S. Pat. No. 5,391,199 to Ben-Haim, the above-referenced European Patent 0 776 176 to Ben-Haim et al., co-pending U.S. patent application Ser. No. 10/029,473, filed Dec. 21, 2001, entitled, "Wireless position sensor," and/or in co-pending U.S. patent application Ser. No. 10/029,595, also filed Dec. 21, 2001, entitled, "Implantable and insertable tags," all of which are assigned to the assignee of the present patent application and are incorporated herein by reference. Alternatively or additionally, substantially any other suitable type of position/coordinate sensing device known in the art is used for position sensing. Still further alternatively or additionally, catheter 20 is marked with one or more markers whose positions can be determined from outside of the body. Suitable markers include radio-opaque markers to facilitate fluoroscopic measurements. Preferably, position-sensing techniques are used that achieve continuous generation of up to six dimensions of location and orientation information with respect to position sensor 30.

Typically, catheter system 10 further comprises a set of external radiators 36, which are adapted to be located at respective positions external to the subject in a vicinity of area of interest 25. For some applications, radiators 36 are adapted to generate fields, such as electromagnetic fields, towards position sensor 30, which is adapted to detect the fields. Alternatively, position sensor 30 generates fields, which are detected by radiators 36. For some applications, a reference position sensor, typically either on an externally-applied reference patch attached to the exterior of the body of the subject, or on an internally-placed catheter, is maintained in a generally fixed position relative to area of interest 25. By comparing the position of catheter 20 to that of the reference catheter, the coordinates of catheter 20 are accurately determined relative to the area of interest, irrespective of motion of the subject. Alternatively, any other suitable method may be used to compensate for such motion.

During a medical procedure, catheter 20 is inserted into area of interest 25. Console 24 typically generates a map 37 of the area of interest. For example, techniques may be used that are described in the above-cited U.S. Pat. Nos. 6,226,542 and 6,301,496 to Reisfeld, European patent application EP 1 125 549 and corresponding U.S. patent application Ser. No. 09/506,766 to Ben-Haim et al., and/or co-pending U.S. patent application Ser. No. 09/598,862 to Govari, all of which are incorporated herein by reference, adapted for use with the techniques described herein. Alternatively, techniques known in the art, e.g., imaging modalities, are used for generating map 37. Map 37 is displayed on monitor 26 with an indication of the location of distal tip 34 of catheter 20 superimposed upon it, typically using position information generated from position sensor 30.

In an embodiment of the present invention, computer 28 calculates potential positions in a vicinity of the current position of distal tip 34, to which the distal tip can be repositioned. These potential positions are designated on map 37. A user of the system points a cursor at or in a vicinity of one of these potential positions, using a computer pointing device such as a mouse, keyboard, joystick or touch sensitive screen. Computer 28 drives control mechanism 22 to position distal tip 34 at the desired position.

For some applications, in order to drive control mechanism 22, computer 28 implements an algorithm that uses an iterative process to direct distal tip 34 to the desired position, responsive to position information generated by position sensor 30 at each iteration. By continuously checking the location of distal tip 34 and appropriately driving the control mechanism 22, the computer precisely controls the location of distal tip 34, regardless of the particular structure of catheter 20 or characteristics of the tissue surrounding catheter 20 at any given time. Additionally, for some applications, computer 28 uses information generated during the iterative process concerning location and motion of distal tip 34, to perform continuous real-time calibration of the system, thus ensuring reliability and accuracy of the system regardless of the character of the tissue through which the catheter is being guided.

Figure 2:
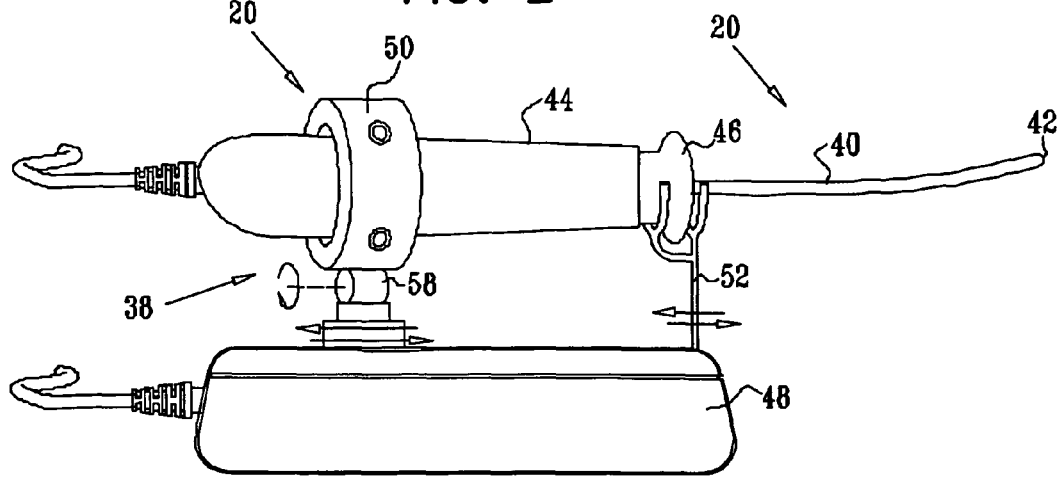
FIG. 2 is a schematic illustration of a robotic control mechanism, in accordance with an embodiment of the present invention.

Reference is now made to FIG. 2, which is a schematic illustration of a robotic control mechanism 38 attached to catheter 20, in accordance with an embodiment of the present invention. In this embodiment, catheter 20 comprises a human-controllable steerable catheter 40 capable of being manually manipulated by a surgeon, such as catheters that are widely commercially available and used today. Catheter 40 comprises manually-controllable means for deflecting a distal tip 42 of the catheter, such as a control handle 44 and/or a thumb control 46. For example, the catheter may utilize techniques described in one or more of the above-referenced U.S. Pat. Nos. RE 34,502, 3,470,876, 4,920,980, 5,489,270, 5,897,529, 5,938,603, 5,964,757, 6,066,125, 6,123,699, 6,165,139, 6,171,277, 6,183,463, 6,198,974, 6,210,362, 6,210,407, and 6,402,719, and/or in the above-referenced PCT Publication WO 98/43530.

Control mechanism 22 comprises robotic control mechanism 38, which is adapted to hold and manipulate human-controllable catheter 40 so as to induce motions of the manually-controllable means that mimic those caused when the manually-controllable means are adjusted by a hand of a surgeon. Robotic control mechanism 38 comprises a controller 48 and one or more end-effectors, such as a proximal gripper 50 and a distal gripper 52. In the exemplary configuration shown in FIG. 2, proximal gripper 50 is adapted to grip handle 44, to move the handle in distal and proximal directions, and to rotate the handle. Robotic control mechanism 38 comprises a motor 58 or other actuator to induce the rotation of proximal gripper 50 and consequently of catheter 40. (For clarity, some supporting structure is not shown in the figure.) Moving the handle and thumb control 46 in concert in distal and proximal directions causes distal tip 42 of the catheter to advance and withdraw, respectively, while rotating handle 44 generally rotates the distal tip. Distal gripper 52 is adapted to grip thumb control 46, and to move the thumb control in distal and proximal directions, typically while proximal gripper 50 remains stationary, so as to manipulate one or more puller wires that pass through one or more lumens (not shown) of catheter 40. Alternatively, proximal gripper 50 moves while thumb control 46 remains stationary, in order to manipulate the one or more puller wires. Manipulation of the puller wires typically deflects distal tip 42 in an arc. Alternatively, handle 44 and/or thumb control 46 use other techniques known in the art for manipulating catheter 40 and/or deflecting distal tip 42. Adaptations of control mechanism 22 to manipulate and control catheters other than that of the exemplary embodiment shown in FIG. 2 will be apparent to those skilled in the art, having read the present patent application. For example, the control mechanism may be adapted to deflect distal tip 42 independently in x- and y-axes. Typically, but not necessarily, the initial insertion of catheter 40 into area of interest 25 is performed manually by the surgeon, who then attaches the end-effectors of robotic control mechanism 38 to catheter 40.

Figure 3:
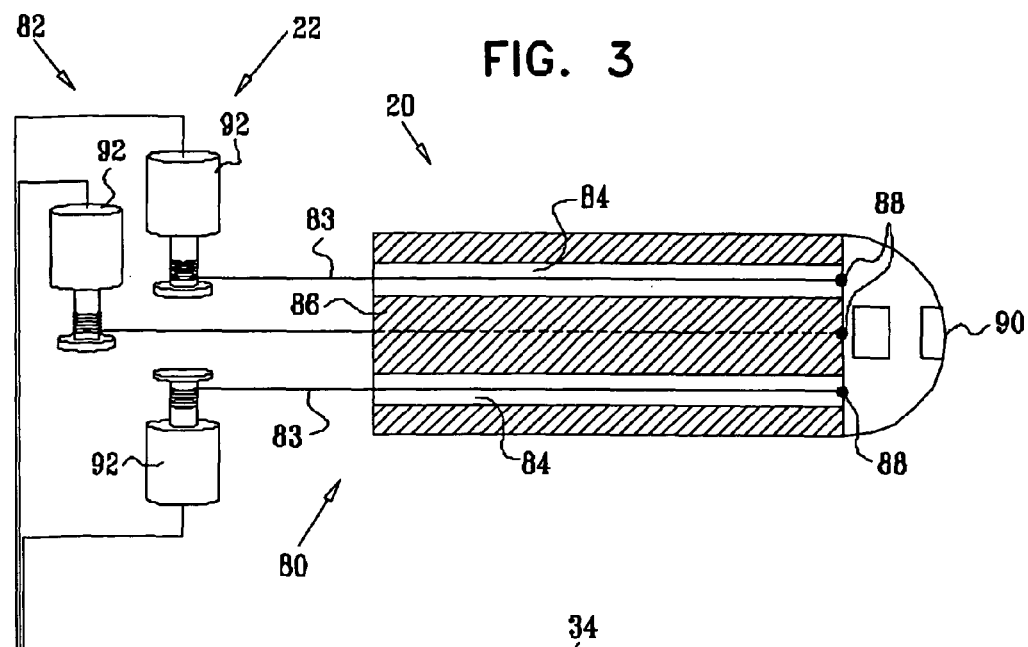
FIG. 3 is a schematic illustration of another robotic control mechanism, in accordance with an embodiment of the present invention.

Reference is now made to FIG. 3, which is a schematic illustration of an integrated robotic control mechanism 82, in accordance with an embodiment of the present invention. In this embodiment, catheter 20 comprises an automated catheter 80, adapted to be primarily robotically controlled. Control mechanism 22 comprises integrated robotic control mechanism 82, which comprises a plurality of puller wires 83, e.g., four. Puller wires 83 are disposed about the circumference of the catheter and extend along its length, passing through respective lumens 84. Typically, the catheter also comprises a spine 86. (Only three of the plurality of puller wires, and two of lumens 84, are shown in FIG. 3 for clarity of illustration.) The distal ends of puller wires 83 are attached at respective points 88 in a vicinity of a distal end 90 of catheter 80, and the proximal ends of the wires are coupled to respective motors 92. Motors 92 are able to tense and relax (or push and pull, depending upon the characteristics of the wire material) the respective puller wires. In this manner, by selective activation of respective motors 92, control mechanism 82 is able to manipulate distal end 90 through 360 degrees of deflection. By applying tension to some or all puller wires 83 simultaneously, control mechanism 82 withdraws catheter 80 in a proximal direction. By extending some or all of the wires and/or by extending spine 86, the control mechanism advances the catheter in a distal direction.

Alternatively or additionally, automated catheter 80 and/or integrated robotic control mechanism 82 utilize robotic control techniques known in the art, for example those described in the above-referenced U.S. Pat. No. 5,078,140, U.S. Pat. No. 5,492,131, US Patent Application Publication 2002/0087151, US Patent Application Publication 2002/0128636, PCT Publication WO 99/45994, and/or PCT Publication WO 02/074178.

In an embodiment of the present invention, integrated robotic control mechanism 82, rather than comprising puller wires 83, comprises a steering mechanism that utilizes shape memory alloys (SMAs), electroactive polymers (EAPs), and/or ionic polymer metal composites (IPMCs). For example, techniques and/or materials may be used that are described in one or more of the above-mentioned U.S. Pat. No. 4,930,494 to Takehana et al., and articles by Kühl C et al., Haga Y et al., Otsuka K et al., Bar-Cohen Y, Bar-Cohen Y et al., and Razavinejad A.

Figure 4:
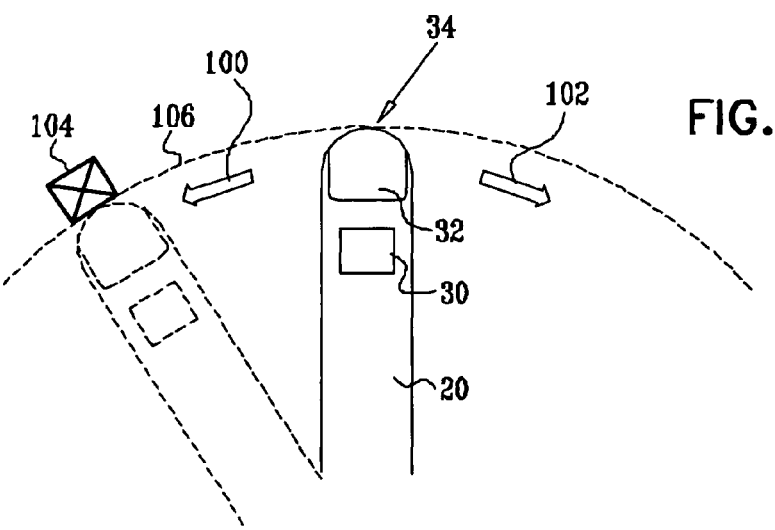
FIG. 4 is a schematic illustration of deflection of a distal tip of a catheter, in accordance with an embodiment of the present invention.

Reference is now made to FIG. 4, which is a schematic illustration of deflection of distal tip 34 of catheter 20, in accordance with an embodiment of the present invention. In this embodiment, position sensor 30 is adapted to generate six dimensions of location and orientation information, typically continuously. Computer 28 (FIG. 1) is adapted to determine the roll of catheter 20 in a vicinity of distal tip 34, by using the six dimensions of information. In this embodiment, control mechanism 22 (FIG. 1) and catheter 20 typically comprise robotic means for deflecting distal tip 34 in either (a) a single direction, as indicated by an arrow 100, for any given roll of the distal tip, or (b) in two opposing directions, as indicated by arrow 100 and an arrow 102, for any given roll of the distal tip. Control mechanism 22 comprises (a) robotic control mechanism 38, described hereinabove with reference to FIG. 2, (b) integrated robotic control mechanism 82, described hereinabove with reference to FIG. 3, or (c) another robotic control mechanism known in the art, including those described in the references cited in the Background of the Invention.

In order to position distal tip 34 at a desired target 104, computer 28 is adapted to drive control mechanism 22 to robotically:

move distal tip 34 into a vicinity of target 104;
roll catheter 20 so that the target intersects a curve 106 defined by the points to which distal tip 34 is able to deflect, given the roll of the distal tip. Computer 28 determines the roll using the six degrees of position information generated by position sensor 30. If necessary, computer 28 additionally drives control mechanism 22 to advance or withdraw distal tip 34 in order to position distal tip 34 so that curve 106 intercepts target 104; and
deflect distal tip 34 to target 104.

Reference is again made to FIG. 1. When control mechanism 22 attempts to roll distal tip 34 of catheter 20, rotation of a proximal end 120 of catheter 20 in a vicinity of control mechanism 22 sometimes does not translate into equivalent roll of distal tip 34. For example, distal tip 34 may sometimes become slightly caught on tissue of area of interest 25. As control mechanism 22 rotates proximal end 120, torque builds up in the catheter, until the torque is sufficient to cause distal tip 34 to come free from the tissue and rotate suddenly.

In an embodiment of the present invention, position sensor 30 is adapted to generate six dimensions of location and orientation information, typically continuously. Computer 28 is adapted to determine the roll of catheter 20 in a vicinity of distal tip 34, by using the six dimensions of information. When computer 28 drives control mechanism 22 to rotate catheter 20, the computer substantially simultaneously determines the roll of distal tip 34, and compares this roll with the expected roll based on the known rotation of proximal end 120 of catheter 20. If the computer detects a lag of the roll of distal tip 34 with respect to the rotation of proximal end 120, the computer drives control mechanism 22 to attempt to move the catheter in order to free distal tip 34 from tissue on which the tip is presumably caught. For example, the computer may drive the control mechanism to:

(a) straighten and/or deflect distal tip 34,
(b) jiggle distal tip 34 until it comes free from the tissue, such as by quickly, repeatedly, rhythmically or irregularly rotating proximal end 120 back and forth by a few degrees,
(c) translationally move the distal tip back and forth, and/or
(d) advance and/or withdraw distal tip 34.

For some applications, computer 28 implements an expert system that evaluates the lag of the roll of distal tip 34 with respect to the rotation of proximal end 120. Responsive to measured or calculated variables, such as the magnitude of the lag and/or the timing of the lag, computer 28 determines which mechanical stimulation to apply to the catheter, the magnitude of such stimulation, and/or the timing of such stimulation. For some applications, the expert system may utilize a lookup table.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a human-controllable steerable catheter comprising a thumb control configured to manually control a deflection of a distal tip of the catheter and a position sensor configured to generate a position signal indicative of six dimensions of location and orientation information, the position sensor fixed in a vicinity of the distal tip of the catheter; and
a robot comprising:
an end-effector coupled to the thumb control; and
a controller configured to drive the end-effector to manipulate in an automated fashion the thumb control in response to the position signal to position the distal tip of the catheter at a desired position based on the six dimensions of location and orientation information.

2. The apparatus according to claim 1, wherein the controller is configured to drive the end-effector to deflect the distal tip by moving the thumb control longitudinally with respect to a longitudinal axis of the catheter.

3. The apparatus according to claim 1,
wherein the catheter includes a handle configured to control a roll of the distal tip,
wherein the robot comprises a handle end-effector coupled to the handle, and
wherein the controller manipulates the handle end-effector to drive the handle to roll the distal tip.

4. The apparatus according to claim 1,
wherein the catheter includes a handle configured to advance and withdraw the catheter,
wherein the robot comprises a handle end-effector coupled to the handle, and
wherein the controller drives the handle end-effector to perform, by manipulating the handle, at least one action selected from the list consisting of: advancing the catheter and withdrawing the catheter.

5. The apparatus according to claim 1, comprising a computer pointing device receiving an indication of a desired position of the distal tip of the catheter.

6. An apparatus comprising:
a human-controllable steerable catheter that includes controls configured to control a deflection of a distal tip of the catheter and a position sensor configured to generate a position signal indicative of six dimensions of location and orientation information, the position sensor being fixed in a vicinity of the distal tip of the catheter, and the controls being generally optimized for manipulation by a human hand; and
a robot comprising:
at least one end-effector coupled to at least a portion of the controls; and
a controller configured to drive the at least one end-effector to deflect the distal tip in response to the position signal by inducing motion of the portion of the controls that generally mimics motion of the portion of the controls induced when a human hand manipulates the controls.

7. The apparatus according to claim 6, wherein the controller is configured to drive the end-effector to deflect the distal tip by moving the portion of the controls longitudinally with respect to a longitudinal axis of the catheter.

8. The apparatus according to claim 6,
wherein the controls are configured to control a roll of the distal tip,
wherein the robot comprises a roll end-effector coupled to the controls, and
wherein the controller is configured to drive the roll end-effector to roll the distal tip by inducing motion of the controls that generally mimics motion of the controls induced when a human hand manipulates the controls.

9. The apparatus according to claim 6,
wherein the controls are configured to advance and withdraw the catheter,
wherein the robot comprises a longitudinal motion end-effector coupled to the controls, and
wherein the controller is configured to drive the longitudinal motion end-effector to perform, by inducing motion of the controls that generally mimics motion of the controls induced when a human hand manipulates the controls, at least one action selected from the list consisting of: advancing the catheter and withdrawing the catheter.

10. The apparatus according to claim 6,
comprising a computer pointing device configured to receive an indication of a desired position of the distal tip of the catheter.

11. Apparatus comprising:
a human-controllable steerable catheter comprising controls configured to manually control a deflection of a distal tip of the catheter and a position sensor configured to generate a position signal indicative of six dimensions of location and orientation information, the position sensor being fixed in a vicinity of the distal tip of the catheter, and the controls being generally optimized for manipulation by a human hand; and
a robot, comprising:
at least one end-effector coupled to at least a portion of the controls; and
a controller configured to drive the end-effector to position the distal tip of the catheter at a desired position based on the six dimensions of location and orientation information by inducing motion of the portion of the controls that generally mimics motion of the portion of the controls induced when a human hand manipulates the controls.

12. Apparatus comprising:
a human-controllable steerable catheter, comprising:
a distal tip configured to be controllably deflectable in no more than two directions for any given rotation of the distal tip, such that a set of all points to which the tip can be deflected at the given rotation forms a deflection curve for the given rotation; and
a position sensor configured to generate a position signal indicative of six dimensions of location and orientation information, the position sensor being fixed in a vicinity of the distal tip; and
a robot configured to manipulate a proximal end of the catheter; and
a control unit configured to:
receive the position signal, and
position the distal tip of the catheter at a target by manipulating the robot in response to the position signal to:
position the distal tip of the catheter in a vicinity of the target, responsive to the position signal based on the six dimensions of location and orientation information,
rotate the proximal end of the catheter in order to cause the distal tip of the catheter to roll to a rotation the deflection curve of which includes the target, the rotation determined responsive to the position signal, and deflect the distal tip of the catheter along the deflection curve to the target.

13. The apparatus according to claim 12, wherein the distal tip is configured to be controllably deflected in no more than one direction for the given rotation of the distal tip.

14. The apparatus according to claim 12, wherein the control unit is configured to position the distal tip in the vicinity of the target by positioning the distal tip so that the deflection curve of at least one rotation of the distal tip includes the target.

15. The apparatus according to claim 12, comprising a computer pointing device configured to receive an indication of a position of the target, wherein the control unit is configured to drive the robot to position the distal tip at the position of the target, responsive to the position signal.

16. Apparatus comprising:
a human-controllable steerable catheter having a distal tip, the catheter comprising a position sensor configured to generate a position signal indicative of six dimensions of location and orientation information, the position sensor being fixed in a vicinity of the distal tip;
a robot configured to be coupled to a proximal end of the catheter; and
a control unit configured to:
drive the robot to apply rotation to the proximal end of the catheter,
receive the position signal,
responsive to the six dimensions of location and orientation information of the position signal, determine a roll of the distal tip of the catheter, and
responsive to a determination that the roll lags the rotation, drive the robot to move a portion of the proximal end of the catheter.

17. The apparatus according to claim 16, wherein the control unit is configured to drive the robot to move the portion of the proximal end of the catheter to perform at least one action selected from the list consisting of: straightening the distal tip and deflecting the distal tip.

18. The apparatus according to claim 16, wherein the control unit is configured to drive the robot to move the portion of the proximal end of the catheter to effect translational back and forth motion of the distal tip.

19. The apparatus according to claim 16, wherein the control unit is configured to drive the robot to move the portion of the proximal end of the catheter to perform at least one action selected from the list consisting of: advancing the distal tip and withdrawing the distal tip.

20. The apparatus according to claim 16, wherein the control unit is configured to move the portion of the proximal end of the catheter to jiggle the distal tip.

21. The apparatus according to claim 20, wherein the control unit is configured to jiggle the distal tip by rotating the proximal end of the catheter.

22. A method for use with a human-controllable steerable catheter having a distal tip configured to be controllably deflectable in no more than two directions for any given rotation of the distal tip, such that a set of all points to which the tip can be deflected at the given rotation forms a deflection curve for the given rotation, the method comprising:
receiving a position signal indicative of six dimensions of location and orientation information from a vicinity of the distal tip of the human-controllable steerable catheter; and
robotically positioning, using a robot, the distal tip of the catheter at a target by:
robotically positioning the distal tip of the catheter in a vicinity of the target, responsive to the six dimensions of location and orientation information of the position signal,
robotically rotating a handle control at the proximal end of the catheter in order to cause the distal tip of the catheter to roll to a rotation the deflection curve of which includes the target, the rotation determined responsive to the six dimensions of location and orientation information of the position signal, and
robotically deflecting the distal tip of the catheter along the deflection curve to the target.

23. The method according to claim 22, wherein robotically positioning the distal tip in the vicinity of the target comprises robotically positioning the distal tip so that the deflection curve of at least one rotation of the distal tip includes the target.

24. The method according to claim 22, comprising receiving an indication of a position of the target, wherein robotically deflecting the distal tip comprises robotically deflecting the distal tip to the position of the target, responsive to the position signal.

25. A method for use with a human-controllable steerable catheter having a distal tip and a proximal end, the method comprising:
robotically rotating a handle control at the proximal end of the human-controllable steerable catheter;
receiving a position signal indicative of six dimensions of location and orientation information from a vicinity of the distal tip of the catheter;
responsive to the position signal, determining a roll of the distal tip; and
responsive to a determination that the roll lags the rotation, robotically moving, using a robot, a portion of the proximal end of the catheter, wherein the steps of robotically rotating and robotically moving are performed in an automated fashion.

26. The method according to claim 25, wherein robotically moving the portion of the proximal end of the catheter comprises robotically performing at least one action selected from the list consisting of: straightening the distal tip and deflecting the distal tip.

27. The method according to claim 25, wherein robotically moving the portion of the proximal end of the catheter comprises robotically translating the distal tip back and forth.

28. The method according to claim 25, wherein robotically moving the portion of the proximal end of the catheter comprises robotically performing at least one action selected from the list consisting of: advancing the distal tip and withdrawing the distal tip.

29. The method according to claim 25, wherein robotically moving the portion of the proximal end of the catheter comprises robotically jiggling the distal tip.

30. The method according to claim 29, wherein robotically jiggling the distal tip comprises robotically rotating the proximal end of the catheter.

* * * * *